US00RE35661E

United States Patent [19]

Thill

[11] E Patent Number: Re. 35,661

[45] Reissued Date of Patent: Nov. 11, 1997

[54] SULFONYLUREA HERBICIDE RESISTANCE IN PLANTS

[75] Inventor: Donald C. Thill, Moscow, Id.

[73] Assignee: Idaho Research Foundation, Inc., Moscow, Id.

[21] Appl. No.: 414,449

[22] Filed: Mar. 30, 1995

Related U.S. Patent Documents

Reissue of:

[64] Patent No.: 5,198,599
Issued: Mar. 30, 1993
Appl. No.: 533,497
Filed: Jun. 5, 1990

[51] Int. Cl.[6] ..... A01H 5/00; A01H 5/10; C12N 5/04

[52] U.S. Cl. ..... 800/200; 800/255; 800/DIG. 13; 800/DIG. 71; 435/418

[58] Field of Search ..... 800/200, 230, 800/255, DIG. 13, DIG. 71; 47/58; 435/418

[56] References Cited

U.S. PATENT DOCUMENTS 4,757,011 7/1988 Chaleff et al. ..... 435/172.1

OTHER PUBLICATIONS

Alcocer–Ruthling et al., *Weed Technology* (1992) 6:303–309.

Alcocer–Ruthling et al., *Weed Technology* (1992) 6:858–864.

Amor, R., *Plant Protection Quarterly* (1986) 1:103–105.

Donn et al., *J. Mol. Appl. Genet.* (1984) 2:621–635.

Eberlein et al., *Weed Science* (1996): in review.

Guttieri et al., *Weed Science* (1992) 40:670–676.

Haughn et al., *Mol. Gen. Genet.* (1988) 21:266–271.

Mallory–Smith et al., *Weed Tech.* (1990) 4:163–168.

Mallory–Smith et al., *Hort. Science* (1993) 28:63–64.

Mazur et al., Nato ASI Ser. A., vol. 140, *Plant Mol. Biol.*, eds., pp. 339–349.

Michelmore et al., *Plant Cell Reports* (1987) 6:439–442.

Reed et al., *Brighton Crop. Prot. Conf.–Weeds* (1989) 1:295–300.

Saari et al., in:*Herbicide Resistant Plants: Biology and Biochemistry*, eds. S. Powles & J. Holtum (1994), pp. 83–139.

*Primary Examiner*—David T. Fox
*Attorney, Agent, or Firm*—Rae-Venter Law Group, P.C.

[57] ABSTRACT

Plants, plant tissues and plant seeds which are resistant to inhibition by sulfonylurea and/or imidazolinone herbicides are provided. In particular, domestic lettuce varieties having resistance to herbicides which target the enzyme acetolactate synthase are provided. The resistant plants find use in areas where weed growth is controlled by sulfonylurea and/or imidazolinone herbicides.

8 Claims, No Drawings

SULFONYLUREA HERBICIDE RESISTANCE IN PLANTS

Matter enclosed in heavy brackets [ ] appears in the original patent but forms no part of this reissue specification; matter printed in italics indicates the additions made by reissue.

INTRODUCTION

Technical Field

This invention relates to plants, plant tissues and seeds, and methods for their preparation, having increased tolerance to herbicides. In particular, the invention involves production of crops which are resistant to sulfonylurea and/or imidazolinone herbicides.

BACKGROUND

Selective herbicides are routinely applied to control weeds among crop plants. The weeds would otherwise compete for available nutrients, water, and light, and thus reduce crop yield and quality. Selective herbicides which show low toxicity to crop species, while playing an important role in the control of weeds in modern agriculture, are often available for only the major crop species because of the high cost of development.

An alternative to the identification of new selective herbicides for use with particular crop species is the genetic modification of susceptible crop species so that they are resistant to non-selective herbicides. One method of achieving this is through the genetic transformation of plants to herbicide resistance. The prerequisites for such an approach are the ability to transform the species of interest, and availability of a gene which confers resistance to the herbicide of interest.

Resistance to a specific herbicide may be a result of introduction into a plant of a gene conferring resistance to the herbicide or may be as a result of long periods of exposure to the herbicide. The resistance may be the result of changes in enzymes which are involved in particular biosynthetic pathways. For example, the broad spectrum weed killer glyphosate (phosphonomethylglycine) acts by inhibiting the enzyme 5-enolpyruvyl-3-phosphoshikimate synthetase that converts phosphoenolpyruvate and 3-phosphoshikimaic acid to 5-enolpyruvate-3-phosphoshikimaic acid in the shikimic acid pathway in bacteria. Following mutagenesis of Salmonella typhimurium, an altered synthetase enzyme resistant to glyphosate has been identified and introduced into plants where it confers resistance to glyphosate.

It is of interest to identify other biosynthetic pathways which may be affected by specific herbicides as a means of developing herbicide resistant plants. Two unrelated classes of herbicides, the sulfonylureas and the imidazolinones, notable for their high herbicidal potencies and low mammalian toxicities, target the enzyme acetolactate synthase, the first common step in the biosynthesis of the essential amino acids isoleucine, leucine and valine, and inhibit plant growth by inactivating the target enzyme. The selective toxicity to weeds of these compounds or their analogs is due to their metabolism by particular crop species but not by most weed species. Thus, for those crop species sensitive to sulfonylureas and imidazolines, it would be of interest to develop crop hybrids or varieties having resistance to these herbicides.

Relevant Literature

Chaleff et al., Molecular Strategies For Crop Protection (1987) pp: 415–425 (Ellen R. Liss Inc. 1987) is an overview of general methods used for developing sulfonylurea herbicide resistant plant varieties. Haughn et al., Molecular General Genetics (1988) 211:266–271 disclose transgenic tobacco plants having resistance to chlorsulfuron as a result of transformation with a gene encoding acetolactate synthase. Mazur et al., Plant Physiol. (1987) 85:1110–1117 and Lee et al., The EMBO Journal (1988) 7:1241–1248 disclose the isolation and characterization of plant genes coding for acetolactate synthase. Chaleff et al., Molecular General Genetics (1987) 210:33–38 disclose two isozymes of acetolactate synthase in tobacco plants resistant to chlorsulfuron and sulfometuron methyl. Ray, Plant Physiol. (1984) 15:827–831 discloses that the site of action of chlorsulfuron is the enzyme acetolactate synthase. U.S. Pat. No. 4,761,373 discloses herbicide resistant maize plants, plant tissues and plant seeds having altered acetohydroxyacid synthase enzymes.

Sulfonylurea resistance has been reported in natural populations of prickly lettuce (Lactuca serriola L.), kochia (Kochia scoparai L.), Russian thistle (Salsola iberica Sennen and Pau, Thill et at. Proc. Weed Sci. Soc. Am. (198) 29:132, and annual ryegrass (Lolium rigidum Gaudin) (Heap et al., Aust. J. Agric. Res. (1986) 37:149–156). Tolerance to sulfonylurea herbicides due to an increased rate of herbicide metabolism has been reported in corn (Zea mays L.) (Eberlein et al. Weed Science (1989) 37:651–657).

Inheritance of sulfonylurea resistance in the bacterium Salmonella typhimurium (LaRossa et at., J. Bacteriol. (1987) 169:1372–1378; in yeast Saccharomyces cerevisiase (Falco et al., Genetics (1985) 109:21–35); and in the green alga, Chlamydomonas reinhardtii (Hartnett et al., Plant Physiol. (1987) 85:898–901) is due to a dominant mutation. In mutated tobacco (Nicotiana tabacum) plants, sulfonylurea resistance is due to a single, semi-dominant, nuclear mutation (Chaleff et al., Science (1984) 223:1148–1151). In Arabiodopis thaliana, sulfonylurea resistance is due-to a single, dominant, nuclear mutation (Haughn et al., Mol. Gen. Genet. (1986) 204:430–434. Sulfonylurea herbicide resistance in soybean mutants has been reported to be a recessive trait (Sebastian et al., Crop Sci. (1987) 27:948–952) and a dominant or semidominant trait (Sebastian et al., Agronomy Abst. (1988) p. 95).

SUMMARY OF THE INVENTION

Novel plants and seeds, and methods for their preparation, are provided which have enhanced resistance to herbicides which target the enzyme acetolactate synthase. The plants are obtained by introduction of a DNA sequence encoding an altered acetolactate synthase into a plant of interest. The resulting transgenic plants are resistant to the growth and development inhibition by said herbicides at concentrations which normally inhibit the growth and development of the plant of interest. The plants can also be grown to produce seed having the resistance phenotype. The resistant plants find use in areas where weed growth is controlled by herbicides which target the enzyme acetalactate synthase.

DESCRIPTION OF SPECIFIC EMBODIMENTS

In accordance with the subject invention, plants, plant tissues, and seeds as well as methods for their preparation are provided which allow for enhanced resistance to herbicides which target the enzyme acetolactate synthase. The gene encoding an altered acetolactate synthase enzyme, which has decreased sensitivity to inhibition by herbicides which target acetolactate synthase, particularly herbicides characterized as sulfonylureas and imidazolinones is transferred to a desired host plant using conventional crossing techniques. The resultant transgenic plants are then resistant to the sulfonylurea and imidazolinone herbicides at concentrations where the herbicides are used selectively to control weeds.

To incorporate the herbicide resistance into a desired crop plant, a plant comprising an altered acetolactose synthase gene can be crossbred with a susceptible crop plant wherein the resistant biotype is capable of transferring genetic information to the susceptible plant to produce a novel hybrid plant having the desired herbicide resistance trait. In order to obtain transgenic plants having the desired trait in a given plant, it is important to determine the mechanism of genetic control of the herbicide resistance. This requires crossing resistant plants with sensitive plants in studying the pattern of inheritance in segregating generations to ascertain whether the trait is expressed as dominant or recessive, the number of genes involved and any possible interactions between genes if more than one are required for expression. This genetic analysis can be part of the initial efforts to convert sensitive plants to resistant plants.

A conversion process (back crossing) is carried out by crossing an original resistant plant to sensitive plants and crossing the progeny back to the sensitive parent. The progeny from this cross would segregate such that some plants carry the gene responsible for resistance whereas some do not. Plants carrying such genes will be crossed again to the sensitive parent resulting in progeny which segregate for resistance and sensitivity once more. This is repeated until the original sensitive parent has been converted to a resistant plant yet possesses all other important attributes as originally found in the sensitive parent. A separate back-crossing program is implemented for each strain that is to be converted to herbicide resistance.

Subsequent to the back crossing, the new resistant plants and the appropriate combinations of strains which make good commercial hybrids are evaluated for resistance as well as important agronomic traits. Resistant strains and hybrids are produced which are true to type of the original sensitive strains and hybrids. This requires evaluation under a range of environmental conditions where the strains or hybrids will generally be grown commercially. For production of herbicide-resistant plants, it may be necessary that both parents of the hybrid seed be homozygous for the resistant trait. Parental lines of hybrids that perform satisfactorily are increased and used from hybrid production using standard hybrid seed production practices.

The source of plants for cross-breeding purposes is any resistant plant capable of cross-breeding with the plant of interest. Known resistant plants include prickly lettuce, kochia (Kochia scoparia L.)/SCRAD), Russian thistle (Salsosa iberica, Sennen and Pau), chickweed (Stellaria media L.) Vill). Other herbicide-resistant plants which may be used for cross-breeding purposes may be identified, for example, by herbicide failure. Herbicide failure is often attributed to environmental conditions, plant growth stage, and improper use or application of the herbicide. However, if these factors are eliminated, herbicide resistance may explain the lack of weed control.

"Herbicide resistance" is the ability of a biotype to survive herbicide treatment to which the species is normally susceptible. Thus, plants resistant to the herbicide of interest may be identified by the lack of weed control in the presence of the herbicide to which the species is normally susceptible. Resistance is due to a heritable genetic trait in the population. Resistance is not based on the herbicide dosage the resistant plant is able to withstand, but rather the difference in response between the response of the original susceptible population and the response of the new biotype.

Alternatively, recombinant DNA techniques may be used for developing resistant lines of plants. This can be achieved by inserting a DNA sequence coding for an altered acetolactate synthase into a plant cell by means of an expression cassette. The expression cassette will include in the 5'-3' direction of transcription, a transcriptional and translational initiation region; a structural gene encoding an altered acetolactase synthase; and a transcriptional and translational termination regulatory region. The initiation and termination regulatory regions are functional in the intended host plant cell and may be either homologous (derived from the original host), or heterologous (derived from a foreign source, or synthetic sequences).

Where recombinant DNA techniques are to be used to obtain the resistant biotype, DNA sequences encoding an altered acetolactase may be obtained in a variety of ways. They may be derived from resistant plants (see above) but may be derived from other eukaryotic sources such as the yeast Saccharomyces cerevisiae and prokaryotes such as Salmonella typhimurium. The altered acetolactate synthase structural gene may be derived from cDNA, from chromosomal DNA or may be synthesized in whole or in part. For the most part, some or all of the structural gene will be from a natural source. Methods for identifying genes of interest have found extensive exemplification in the literature, although in individual situations different degrees of difficulty may be encountered. Various techniques include the use of probes where genomic or cDNA libraries may be searched for complementary sequences.

The gene may be synthesized in whole or in part, particularly where it may be desirable to modify all or a portion of the codons, for example to enhance expression, by employing host-preferred codons. Thus, all or a portion of the open reading frame encoding the altered acetolactate synthase may be synthesized using codons preferred by the plant host. Plant-preferred codons may be determined from the codons of highest frequency and the proteins expressed in the largest amount in the particular plant species of interest.

Methods for synthesizing sequences and bringing the sequences together are well established in the literature. Where a portion of the open reading frame is synthesized, and a portion is derived from natural sources, the synthesized portion may serve as a bridge between two naturally-occurring portions, or may provide a 3'-terminus or a 5'-terminus. Particularly where the transcriptional initiation region and the open reading frame encoding the altered acetolactase synthase are derived from different genes, synthetic adaptors commonly will be employed. In other instances, polylinkers may be employed, where the various fragments may be inserted at different restriction sites or substituted for a sequence in the polylinker.

If the structural gene to be inserted is derived from prokaryotic cells, it is desirable to minimize this 3' non-coding region of the prokaryotic gene. The substantial absence of this region can have a positive effect on the transcription, the stability, and/or translation of the mRNA in the host plant cells. In order to have expression of a gene other than a plant gene in a plant cell, transcriptional and translational initiation regulatory regions functional in a plant cell must be provided. Promoters and translation initiation signals functional in plant cells include those from genes which are present in the plant host or other plant species, for example the ribulose biphosphate carboxylase small subunit transcriptional initiation region, for example from tobacco; those present in viruses, such as the cauliflower mosaic virus (CaMV), for example the 35S transcriptional initiation region; and those associated with T-DNA such as the opine synthase transcriptional initiation regions, for example, octopine, manopine, agropine, and the like.

Regulatory regions may be homologous or heterologous to the plant host. In order to join the promoter to the structural gene, the noncoding 5' region upstream from the structural gene may be removed by endonuclease restriction. Alternatively, where a convenient restriction site is present near the 5' terminus of the structural gene, the structural gene may be restricted and an adaptor employed for linking the structural gene to a promoter region where the adaptor provides the missing nucleotides of the structural gene.

The termination region may be derived from the 3' region of the gene from which the initiation region was obtained or from a different gene. The termination region may be derived from a plant gene, particularly the tobacco ribulose biphosphate carboxylase small subunit termination region; a gene associated with the Ti-plasmid such as the octopine synthase termination region; or the tml termination region.

In developing the expression cassette, the various fragments comprising the regulatory regions and open reading frame may be subjected to different processing conditions, such as ligation, restriction enzyme digestion, resection, in vitro mutagenesis, primary repair, use of linkers and adaptors, and the like. Thus, nucleotide transitions, transversions, insertions, deletions or the like, may be performed on the DNA which is employed in the regulatory regions and/or reading frame. The expression thus may be wholly or partially derived from natural sources, and either wholly or partially derived from sources homologous to the host cell, or heterologous to the host cell. Furthermore, the various DNA constructs (DNA sequences, vectors, plasmids, expression cassettes) of the invention are isolated and/or purified or synthesized and thus are not "naturally occurring."

The expression cassette will normally be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed plant cells as compared to plant cells lacking the DNA of interest.

During the construction of the expression cassette, the various fragments of the DNA will usually be cloned in an appropriate cloning vector, which allows for amplification of the DNA, modification of the DNA or manipulation by joining or removing of sequences, linkers or the like. Normally the vectors will be capable of replication and at least a relatively high copy number in E. coli.

Plants of interest include crops whose cells or explants can be manipulated and subjected to selection and regeneration in tissue culture. The appropriate candidates for transformation with a gene conferring resistance to herbicides characterized as sulfonylureas and imidazolinones. It is contemplated that any plant variety having the above characteristics would constitute a suitable host plant. Of particular interest are plants of the family composite including sun flower lettuce, safflower.

A variety of techniques are available for the introduction of DNA into the plant cell host. These techniques include transformation with T-DNA, employing Agrobacterium tumefaciens or Agrobacterium rhizogenes as the transforming agent, protoplast fusion, injection, electroporation, etc. The transformation with agrobacteria is commonly with plasmids which contain DNA homologous with the Ti-plasmid, particularly T-DNA, which can be prepared in E coli.

The plasmid may or may not be capable of replication in Agrobacteria, that is, it may or may not have a broad spectrum prokaryotic replication system, for example, rk290, depending in part upon whether the expression cassette is to be integrated into the Ti-plasmid or to be retained on an independent plasmid. By means of a helper plasmid, the transcription construct may be transferred to the Agrobacterium and the resulting transformed organism used for transforming plant cells. The use of T-DNA for transformation of plant cells has received extensive study and is, for example, described in EPA Serial Number 120,516, Hockema, in: The Binary Plant Vector System, Offsetdrukkerij Kanters BV, Alblasserdam, 1985; Chapter V, Kanaf et al., "Genetic Analysis of Host Range Expression by Agrobacterinm," in Molecular Genetics of the Bacteria - Plant Interaction" Puhler A. Ed. Springer Verlag, New York (1983) p 245, and An et al., EMBO Journal (1985) 4:277–284.

After transformation, the cell tissue (for example protoplasts, explants, or cotyledons) is transferred to a regeneration medium, such as Murashige-Skoog (MS) medium for plant tissue and cell culture, for formation of a callus. Cells that have been transformed may be grown into plants in accordance with conventional ways. See for example, McCormick et al., Plant Cell Reports (1986) 5:81–84.

Transformed plants may be analyzed to determine whether the desired gene product is being produced in or a portion of the plant cells. After expression of the desired product has been demonstrated in the plant, these plants may then be grown, and either pollinated with the same transformed strain or different strains, and the resulting hybrid having the desired phenotypic characteristic(s) identified. Two or more generations may be grown to ensure that the subject phenotypic characteristic is still being maintained and inherited. Seeds may then be harvested for use to provide plants having the new phenotypic property, namely resistance to herbicides which target the acetolactate synthase enzyme.

Various techniques exist for determining whether the desired DNA sequences are present in the plant cell and are being transcribed. Techniques such as the Northern Blot can be employed for detecting messenger RNA which codes for rhiticide herbicide. In addition, the presence of expression can be detected by identifying the altered enzyme, including solution enzyme assay, estrin analysis and native electrophoresis with activity staining. Furthermore, anti-bodies specific for the altered enzyme may be employed.

The transgenic plants can be evaluated directly, for example, transgenic plants can be evaluated for resistance to the herbicide of interest, particularly sulfonylurea and imidazolinone herbicides. By the ability of the plant to grow in the presence of higher concentrations of the herbicide as compared to non-transgenic plants, or plants transformed with other than an expression cassette providing for herbicide resistance.

Plants engineered to produce an altered acetolactate synthase find use in being able to grow under conditions where sulfonylurea and imidazolinone herbicides are used to selectively control weeds.

The following examples are offered by way of illustration and not by way of limitation.

EXPERIMENTAL

Sulfonylurea resistant prickly lettuce (Lactuca serriola) seeds were deposited with the American Type Culture Collection, 12301 Parklawn Drive, Rockville, Md. 20852, on May 29, 1990 and have received accession number 40815.

EXAMPLE 1

Identification of Sulfonylurea Herbicide-Resistant Prickly Lettuce

In the spring of 1987, a field study was established 15 km south of Lewiston, ID in response to a grower's complaint that *in* 1986 a fall-applied 5:1 formulated mixture of chlorsulfuson [2-chloro-N-[[CH-methoxy-6-methyl-1,3,5-triazin-2-yl-amino]carbonyl]benzenesulfonamide]:metsulfuron [2-[(L-4-methoxy-6-methyl-1,3,5-triazin-2-yl)amino]carbonyl] E. I. dupont de Nemours & Company, Inc.) (26 g ai/ha) failed to control prickly lettuce in winter wheat. The grower also noted prickly lettuce had not been controlled effectively in the previous winter wheat crop with 16 g/ha chlorosulfuron:metsulfuron (DPX-G8311). The cropping system on this farm had been continuous no-till winter wheat since 1983. Chemical fallow was used in rotation with winter wheat on some of the fields, but fields with shallow soil (<60 cm) were cropped each year.

Wheat had been the only crop produced for the past 30 years. Average rainfall for the farm was 36 to 46 cm/year. The grower had used sulfonylurea herbicides since 1982 for both chemical fallow and weed control in winter wheat. Weed scientists from the University of Idaho had experimented with herbicide efficacy on this farm for more than 12 years. Sulfonylurea herbicides first were applied in 1980 experiments. (Handly et al., "Wild Carrot and Broadleaf Weed Control in Winter Wheat," Idaho Feed Control, Report 9 (1980).) Often the experimental rates, for example 137 g ai/ha chlorsulfuron in the 1980 study (ibid), were much higher than the final labeled rate; so actual amount of herbicide applied to some fields was greater than was shown by the grower's field records. The grower applied sulfonylurea herbicides at intervals ranging from 6 to 14 months (See Table 1 below).

TABLE 1

Field History and Edaphic Information for the Farm Where Sulfonylurea (SU) Resistant Prickly Lettuce Initially was Reported

| Field Number | Size (ha | Soil pH | Soil Organic Matter (%) | First Year Treatment (SU) | Maximum SU[a] (g ai/ha) | Interval[b] (months) |
|---|---|---|---|---|---|---|
| 1 | 167 | 5.7 | 3.2 | 1982 | 151 | 7 |
| 2 | 54 | 5.4 | 3.8 | 1982 | 153 | 9 |
| 3 | 88 | 6.7 | 3.8 | 1983 | 52 | 14 |
| 4 | 43 | 6.4 | 2.8 | 1983 | 100 | 9 |
| 5 | 97 | 5.7 | 3.1 | 1982 | 96 | 9 |
| 6 | 22 | 5.7 | 2.9 | 1982 | 114 | 8 |
| 7 | 23 | 64 | 2.7 | 1982 | 148 | 9 |
| 8 | 37 | 5.1 | 4.0 | 1982 | 137 | 7 |
| 9 | 90 | 6.2 | 4.1 | 1982 | 200 | 6 |

[a]Maximum ai/ha that was applied in this field. All areas in the field may not have received the maximum.
[b]Months between herbicide applications.

Field Studies 1. 1987 Study. Field plots were established Apr. 14, 1987, and Apr. 20 and 26, 1988 to determine if this prickly lettuce biotype would resist sulfonylurea herbicides. The experimental design for all studies was a randomized complete block with four replications. Plots were 3 by 9 m. Treatments were applied with a $CO_2$ pressurized backpack sprayer calibrated to deliver 90 L/ha at 275 kPA and 4.8 km/h. Sulfonylurea herbicides were applied with a nonionic surfactant (octyl phenoxy polyethoxy ethanol, 90% ai) at 0.25% vv. The soil was a silt loam with a pH of 4.9, 3.9% organic matter, and a cation exchange capacity (meg/100 g soil) of 21.

In 1987, the sulfonylurea treatments were Thifensulfuron DPX-G8311, and a 2:1 formulated mixture of thifensulfuron (Dupont) {3-[[[[(4-methoxy-6-methyl-1,3,5,triazin-2-yl)amino]carbonyl]amino]sulfonyl]-2-thiophenecarboxylic acid}:DPX-L5300 (Dupont) {methyl-2-[[[[N-(4-methoxy-6-methyl-1,3,5-triazin-2-yl)methylamino]carbonyl]amino]sulfonyl]benzoate} at 13, 26, and 52 g ai/ha. Thifensulfuron:DPX-L5300 is numbered DPX-R9674 (Dupont). The other two herbicide treatments were the butoxyethyl ester of 2,4-D [(2,4-dichlorophenoxy)acetic acid] and the octanoic acid ester of bromoxynil (3,5-dibromo-4-hydroxybenzonitrile) plus the isooctyl ester of MCPA [(4-chloro-2-methylphenoxy)acetic acid] at 840 and 430 g ae/ha, respectively. There were 200 to 400 prickly lettuce plants per $m^2$ at the time of herbicide application. Percent control was evaluated visually five times during the growing season. On July 6, plants in a 0.37 $m^2$ quadrant were counted. The shoots were harvested, dried for seven days at 60° C., and then weighed.

Neither of the sulfonylurea herbicides at any application rate controlled more than 10% of the prickly lettuce, while the 2,4-D and bromoxynil plus MCPA treatments controlled 100% of the prickly lettuce. The number of prickly lettuce plants (range 168 to 316 $m^2$ or weight per prickly lettuce plant (range 1410 to 2270 mg) in the sulfonylurea treated plots was not significantly different from plant number (292 $m^2$) or weight (1600 mg) in the control plots.

2. 1988 Study. In 1988, two field studies similar to the 1987 study were established in the same field. There were 100 prickly lettuce plants per $m^2$ at the time of treatment. Prickly lettuce control was evaluated visually May 20.

The herbicides used in study 1 were DPX-G8311, DPX-R9674, 2,4-D, bromoxynil, diuron [N'-(3,4-dichlorophenyl)-N,N-dimethylurea) and CGA-131036 [N-(6-methoxy-4-methyl-1,3,5-triazin-2-yl-aminocarbonyl-2-(2-chloroethoxy)benzene-sulfonamide]. DPX-G8311 and DPXR9674 were applied at 16 and 26 g/ha alone and in tank mixes with the other herbicides except CGA-131036 which was applied alone at 26 g ai/ha. Diuron, bromoxynil, and 2,4-D were applied alone at 670, 430, and 840 g/ha, respectively. These same rates as well as diuron at 340 g/ha, bromoxynil at 220 g/ha, and 2,4-D at 420 g/ha were included in the tank mixes with 16 and 26 g/ha of both DPX-G8311 and DPX-R9674.

Study 2 also included herbicides alone and in Btank mixes. Herbicides in this study were DPX-G8311, diuron, MCPA, CGA-131036, the potassium salt of picloram [4-amino-3,5,6-trichloro-2-pyridinecarboxylic acid], the dimethylamine salt of dicamba [3,6-dichloro-2-methoxybenzoic acid], and the alkanolamine salt of clopyralid [3,6-dichloro-2-pyridinecarboxylic acid] plus the alkanolamine salt of 2,4-D. DPX-G8311 at 16 g/ha was applied alone and in a tank mix with 18 g ae/ha picloram. Clopyralid plus 2,4-D was applied alone at 450 and 670 g ae/ha and at 450 g/ha with 450 g/ha MCPA. MCPA and 2,4-D were each applied alone at 840 g/ha. They both were applied at two rates, 280 and 420 g/ha, as tank mixes with 18 and 26 g/ha picloram. Picloram at 18 and 26 g/ha was tank mixed with 70 and 140 g/ha dicamba.

The results of the 1988 field studies were the same as those of the 1987 study. In Study 1, neither DPX-G8311 nor DPX-R9674 controlled prickly lettuce. CGA-131036 controlled only 30% of the prickly lettuce, while all other herbicides controlled at least 86% of the weed. When sulfonylurea herbicides were tank mixed with the other broadleaf herbicides, prickly lettuce control did not increase.

In Study 2, DPX-G8311 alone did not control prickly lettuce, while all other treatments, either alone or in tank mixes, controlled at least 98% of the prickly lettuce. When DPX-G8311 was tank mixed with picloram, the same level of control as achieved with picloram alone was observed.

Results from these field experiments show this bio-type of prickly lettuce was not controlled with sulfonylurea herbicides. In field studies conducted during the 1983–1984 winter wheat growing season, at the same location as the 1987 and 1988 field studies, thifensulfuron plus either metsulfuron or chlorsulfuron controlled 100% of the prickly lettuce in the treated plots (Schaat et al., "Broadleaf weed control in winter wheat," Res. Prog. Rep. West. Soc. Weed Sci. (1985) pp 320–321). The sulfonylurea-resistant biotype of prickly lettuce likely was selected because sulfonylurea herbicides were used frequently in a continuous winter wheat production system. Other herbicides with different mechanisms of action and known to control prickly lettuce control the resistant biotype effectively.

Field Survey. On Apr. 3, 1988, 153 representative plants were randomly selected from 51 locations in the 9 fields. Seedlings in the 2 to 3 leaf stage were dug, transplanted into 580-ml styrofoam cups, and then transported to the University of Idaho greenhouses. Seedlings were treated Apr. 21, 1988, with 30 ml of 500 ppb w/v metsulfuron as a combination foliar application and soil drench. This concentration is five times the concentration required to reduce plant growth of the susceptible biotype by 90% (see Greenhouse Studies). Plants were evaluated visually as resistant (alive with normal or near-normal growth) or susceptible (dead) May 2 and again May 9, 1988.

Of the 153 plants collected, 43% resisted 500 ppb metsulfuron (Table 2).

TABLE 2

The Percentage of Prickly Lettuce Plants in the Field Survey Showing Resistance to Metsulfuron at 500 ppb w/v

| Field[a] | Plants (no.) | Resistant (%) |
|---|---|---|
| 1 | 30 | 70 |
| 2 | 9 | 56 |
| 3 | 15 | 53 |
| 4 | 12 | 67 |
| 5 | 27 | 0 |
| 6 | 12 | 8 |
| 7 | 6 | 83 |
| 8 | 15 | 0 |
| 9 | 27 | 48 |
| Total | 153 | |
| mean = | 43 | |

[a]See Table 1 for field description.

Only 2 of the 9 fields surveyed had no resistant plants, indicating that the resistant biotype was spread over most of the cultivated areas of the farm. Since prickly lettuce seeds can be dispersed by wind, environmental and geographical factors may explain why no resistant plants were found in Fields 5 and 8. Field 5 was located at the west edge of the farm, and the prevailing winds are away from the field. Field 8, near the middle of the farm, was isolated by terrain. It was lower in elevation and had a rock bluff on the west edge.

Noncultivated areas of the farm and areas bordering the farm are being surveyed for the resistant biotype. Preliminary results of this survey indicate the resistant biotype is contained on the cultivated areas of the farm. However, resistant plants have been found on roadsides and disturbed areas 2 km from the farm.

Greenhouse Studies. Seeds were gathered during August and September 1987 from three sites: the field plot area south of Lewiston and untreated sites near Troy and Moscow, Id. All three selections were ascertained to be prickly lettuce by a University of Idaho plant taxonomist. Preliminary studies showed the Troy and Moscow selections were equally susceptible to metsulfuron; therefore, the selections were used interchangeably in the studies. Seeds were planted in commercially prepared potting mix (Sunshine Mix #1. Fisons West corp., 1212 W. Broadway, Vancouver, B.C. Canada B6H3B1) in 440-ml styrofoam cups in the greenhouse. Seedlings were thinned to two per cup at the 2- to 3-leaf stage and were treated with 30 ml of metsulfuron herbicide solution as a combination foliar application and soil drench. A nonionic surfactant (same as in the field studies) at 0.25% v/v was added to all herbicide treatments. Metsulfuron concentrations were 1, 5, 10, 50, 100, 500, and 1000 ppb ai w/v. The experimental design was a randomized complete block with four replications repeated three times. Ten days after treatment, plant shoots were harvested and leaf areas measured with a leaf area meter (Li-COR Model LI 3000. LI-COR, Inc., P.O. Box 4425, Lincoln, Nebr. 68504). The plant shoots then were dried for 48 hours at 50° C. and weighed.

Two studies were conducted to determine resistance to seven other sulfonylurea herbicides using the prickly lettuce seed collected near Lewiston (resistant) and Troy (susceptible). Sulfonylurea herbicides included in Study 1 were CGA-131036, chlorsulfuron, and DPX-L5300. Study 2 included the sulfonylurea herbicides bensulfuron {2-[[[[[(4-6-dimethoxy-2-pyrimidinyl)amino]-carbonyl]amino]sulfonyl]methyl]benzoic acid}, chlorimuron {2-[[[[(4-chloro-6-methoxy-2-pyrimidinyl)amino]carbonyl]-amino]sulfonyl]benzoic acid}, thifensulfuron, and sulfometuron {2[[[[(4,6-dimethyl-2-pyrimidinyl)amino]carbonyl]amino]sulfonyl]benzoic acid}. Metsulfuron was included as a reference in all experiments. Herbicide concentrations used in these experiments were 10, 100, and 1000 ppb ai w/v.

Resistance experiments were repeated twice. Experimental design was a randomized complete block with three replications. Plants were harvested, and leaf area and dry weight were determined as described previously.

Cross resistance to three imidazolinone herbicides, imazapyr={(+)-2-[4,5-dihydro-4-methyl-4-(1-methylethyl)-5-oxo-1H-imidazole-2-yl]-3-pyridinecarboxylic acid}, imazaquin={2-[4,5-dihydro-4-methyl-4-(1-mythelethyl)-5-oxo-1H-imidazole-2-yl]-3-quinolinecarboxylic acid}, and imazethapyr={(+)-2-[4,5-dihydro-4-methyl-4-(1-methylethyl)-5-oxo-1H-imidazole-2-yl]-5-ethyl-3-pyridinecarboxylic acid)} was examined, since this class of herbicides has the same site of action as the sulfonylurea herbicides (Shaner et al., "Imidazolinones: Potent inhibitors of acetohydroxyacid synthase," Plant Physiol. (1984) 76:545546). The experimental design was the same as the sulfonylurea herbicide resistance studies, except only one seedling was left per cup; and herbicide concentrations were 500, 1000, 2500, 5000, 10000, and 25000 ppb ai w/v. Plant shoots were harvested 14 days after treatment, and leaf area and dry weight were measured.

Regression analysis was used to compute a 50% growth reduction (GR50). Analysis of variance was used to calculate Least Significant Differences (LSD) in leaf area and dry weight as well as to determine interactions among variables. Pearson correlation coefficients (Snedecor et al., Statistical Methods, 7th Ed. Iowa State University Press, Ames (1980) p 192) were computed between leaf area and dry weight.

The Pearson correlation coefficient between leaf areas and dry weight was high (0.9); therefore, only leaf area data are reported. Herbicide concentrations required for $GR_{50}$ values were calculated using regression; however, in most cases, a $GR_{50}$ was not reached for the resistant biotype.

TABLE 3

Leaf Area and Percent of Control Leaf Area for Susceptible and Resistant Biotypes of Prickly Lettuce Treated with Eight Concentrations of Metsulfuron in the Greenhouse

| Rate | Biotype | | | |
|---|---|---|---|---|
| | Susceptible | | Resistant | |
| (ppb w/v) | ($cm^2$) | (% of Control) | ($cm^2$) | (% of Control) |
| 0 | 104 | 100 | 12 | 100 |
| 1 | 78 | 75 | 143 | 117 |
| 5 | 70 | 67 | 123 | 100 |
| 10 | 80 | 77 | 140 | 114 |
| 50 | 15 | 15 | 146 | 119 |
| 100 | 17 | 17 | 122 | 99 |
| 500 | 8 | 8 | 91 | 74 |
| 1000 | 7 | 7 | 60 | 49 |
| LSD (0.05) | 33 | | | 40 |
| LSD (0.05) | | (rate × biotype) 40 | | |

TABLE 4

Leaf Area and Percent of Control Leaf Area for Susceptible and Resistant Biotypes of Prickly Lettuce Treated with Four Sulfonylurea Herbicides at Three Concentrations in the Greenhouse

| | | Biotype | | | |
|---|---|---|---|---|---|
| | | Susceptible | | Resistant | |
| Herbicide | Rate (ppb w/v) | ($cm^2$) | (% of Control | ($cm^2$) | (% of Control) |
| CGA-131036 | 0 | 81 | 100 | 164 | 100 |
| | 10 | 53 | 65 | 191 | 116 |
| | 100 | 8 | 10 | 174 | 106 |
| | 1000 | 8 | 10 | 106 | 65 |
| | LSD (0.05) | 25 | | 53 | |
| | LSD (0.05) | | (rate × biotype) 21 | | |
| Chlorsulfuron | 0 | 85 | 100 | 181 | 100 |
| | 10 | 61 | 72 | 196 | 108 |
| | 100 | 17 | 20 | 194 | 107 |
| | 1000 | 5 | 6 | 164 | 91 |
| | LSD (0.05) | 18 | | ns | |
| | LSD (0.05) | | (rate × biotype) 34 | | |
| DPX-L5300 | 0 | 86 | 100 | 172 | 100 |
| | 100 | 68 | 79 | 176 | 102 |
| | 100 | 11 | 13 | 180 | 105 |
| | 1000 | 6 | 7 | 181 | 105 |
| | LSD (0.05) | 22 | | ns | |
| | LSD (0.05) | | (rate × biotype) 33 | | |
| Metsulfuron | 0 | 88 | 100 | 176 | 100 |
| | 10 | 42 | 48 | 178 | 101 |
| | 100 | 8 | 9 | 170 | 97 |
| | 1000 | 6 | 8 | 69 | 39 |
| | LSD (0.05) | 33 | | 43 | |
| | LSD (0.05) | | (rate × biotype) 37 | | |

TABLE 5

Leaf Area and Percent of Control Leaf Area for Susceptible and Resistant Biotypes of Prickly Lettuce Treated with Five Sulfonylurea Herbicides at Three Concentrations in the Greenhouse

| | | Biotype | | | |
|---|---|---|---|---|---|
| | | Susceptible | | Resistant | |
| Herbicide | Rate (ppb w/v) | ($cm^2$) | (% of Control | ($cm^2$) | (% of Control) |
| Bensulfuron | 0 | 128 | 100 | 152 | 100 |
| | 10 | 132 | 103 | 137 | 90 |
| | 100 | 122 | 95 | 149 | 98 |
| | 1000 | 48 | 37 | 152 | 100 |
| | LSD (0.05) | 45 | | | |
| | LSD (0.05) | | (rate × biotype) 43 | | |
| Chlorimuron | 0 | 126 | 100 | 146 | 100 |
| | 10 | 102 | 81 | 138 | 94 |
| | 100 | 45 | 35 | 112 | 75 |
| | 1000 | 14 | 11 | 81 | 55 |
| | LSD (0.05) | 39 | | | |
| | LSD (0.05) | | (rate × biotype) ns | | |
| Thifen-sulfuron | 0 | 112 | 100 | 149 | 100 |
| | 10 | 132 | 118 | 152 | 102 |
| | 100 | 135 | 120 | 145 | 97 |
| | 1000 | 26 | 23 | 133 | 89 |
| | LSD (0.05) | 28 | | ns | |
| | LSD (0.05) | | (rate × biotype) 40 | | |
| Metsulfuron | 0 | 131 | 100 | 143 | 100 |
| | 10 | 137 | 105 | 148 | 103 |
| | 100 | 57 | 44 | 125 | 87 |
| | 1000 | 7 | 5 | 86 | 60 |
| | LSD (0.05) | 26 | | ns | |
| | LSD (0.05) | | (rate × biotype) 44 | | |
| Sulfometuron | 0 | 132 | 100 | 157 | 100 |
| | 10 | 112 | 85 | 152 | 96 |
| | 100 | 40 | 30 | 157 | 100 |
| | 1000 | 9 | 7 | 147 | 93 |
| | LSD (0.05) | 36 | | ns | |
| | LSD (0.05) | | (rate × biotype) 41 | | |

Therefore, rather than extrapolate a concentration, actual leaf area ($cm^2$) are presented in Tables 3, 4, and 5 as well as leaf area of the treated plants as a percent of the untreated check (0 ppb). LSD mean separation for herbicide concentration within each biotype by herbicide are included in addition to the mean separation for the biotype by concentration interaction.

Fifty percent growth reduction ($GR_{50}$) on the resistant biotype was reached with the highest concentration of metsulfuron, 1000 ppb (Table 3), but not with the other sulfonylurea herbicides (Tables 4 and 5). The concentration required to produce a $GR_{50}$ on the susceptible biotype depended on the sulfonylurea herbicide (Tables 3, 4, and 5). For six of the eight sulfonylurea herbicides tested, the $GR_{50}$ value for the susceptible biotype was between 10 and 100 ppb. Prickly lettuce is less sensitive to bensulfuron and thifensulfuron.

The prickly lettuce response to metsulfuron was similar in all experiments (Tables 3, 4, and 5). For example, in Study 1 (Table 4), the $GR_{50}$ for metsulfuron on the susceptible biotype was between 0 and 10 ppb, while the $GR_{50}$ for metsulfuron on the resistant biotype was between 100 and 1000 ppb. In Study 2 (Table 5), the $GR_{50}$ for the susceptible biotype was between 10 and 100 ppb, while a $GR_{50}$ on the resistant biotype was not reached with metsulfuron. Response to metsulfuron between the two susceptible biotypes, Moscow and Troy did not differ.

The response of the resistant and susceptible biotypes varied among imidazolinone herbicides (Table 6). The $GR_{50}$ values for the resistant biotype treated with imazapyr and imazethapyr were more than 4 times the $GR_{50}$ for the susceptible biotype. Both biotypes were equally affected by imazaquin.

TABLE 6

Leaf Area and Percent of Control Leaf Area Susceptible and Resistant Biotypes of Prickly Lettuce Treated with Three Imidazolinone Herbicides at Six Rates in the Greenhouse

| | | Biotype | | | |
|---|---|---|---|---|---|
| | | Susceptible | | Resistant | |
| Herbicide | Rate (ppb w/v) | ($cm^2$) | (% of Control | ($cm^2$) | (% of Control) |
| Imazapyr | 0 | 152 | 100 | 152 | 100 |
| | 500 | 122 | 80 | 124 | 82 |
| | 1000 | 99 | 65 | 128 | 84 |
| | 2500 | 31 | 20 | 113 | 74 |
| | 5000 | 13 | 9 | 91 | 60 |
| | 10000 | 11 | 7 | 65 | 43 |
| | 25000 | 9 | 6 | 23 | 15 |
| | LSD (0.05) | 49 | | 44 | |
| | LSD (0.05) | | (rate × biotype) 34 | | |
| Imazaquin | 0 | 137 | 100 | 107 | 100 |
| | 500 | 118 | 86 | 119 | 111 |
| | 1000 | 124 | 91 | 85 | 79 |
| | 2500 | 86 | 63 | 51 | 48 |
| | 5000 | 42 | 31 | 26 | 24 |
| | 10000 | 23 | 17 | 21 | 20 |
| | 25000 | 11 | 8 | 13 | 12 |
| | LSD (0.05) | 44 | | 25 | |
| | LSD (0.05) | | (rate × biotype) ns | | |
| Imazethapyr | 0 | 165 | 100 | 158 | 100 |
| | 500 | 168 | 100 | 139 | 88 |
| | 1000 | 137 | 83 | 121 | 77 |
| | 2500 | 90 | 55 | 124 | 78 |
| | 5000 | 83 | 50 | 108 | 68 |
| | 10000 | 47 | 28 | 123 | 78 |
| | 25000 | 28 | 17 | 73 | 46 |
| | LSD (0.05) | 68 | | ns | |
| | LSD (0.05) | | (rate × biotype) ns | | |

Results from these experiments showed the prickly lettuce biotype from Lewiston was resistant to sulfonylurea herbicides. This biotype showed cross resistance to the eight sulfonylurea herbicides tested but not to broadleaf herbicides with different sites of action which were tested. Resistance of a prickly lettuce biotype to sulfonylurea herbicides may or may not indicate resistance to an imidazolinone herbicide. These whole plant responses are similar to results reported by Saxena et al., "Herbicide resistance in Datura Innoxia," Plant Physiol. (1988) 86:863–867 for Datura Innoxia cell culture.

EXAMPLE 2

Incorporating Sulfonylurea Herbicide Resistance into Domestic Bibb Lettuce

1. Bibb Lettuce

Incorporation of sulfonylurea herbicide resistance into domestic Bibb lettuce was accomplished as shown in the following schematic. RPL=sulfonylurea herbicide resistant prickly lettuce; RF or RBC indicate resistant progeny.

RPL x Bibb (January 1988)

↓

-continued $F_1$ (March 1988 treated with 500/ppb metsulfuron)

↓

$RF_1$ x Bibb (May 1988)

↓

$BC_1$ (August 1988 treated with 500 ppb metsulfuron)

↓

$RBC_1$ x Bibb (October–November 1988)

↓

$BC_2$ (January–March treated with 500 ppb metsulfuron or 0.0702 lb ai/a DPX-R9674)

↓

$RBC_2$ x Bibb (April 1989)

↓

$BC_3$ (May–October 1989 0.0702 lb ai/a DPX-R9674)

↓

$RBC_3$ x Bibb (October–November 1989)

↓

$BC_4$ (November 1989 treated with 0.0702 lb ai/a DPX-R9674)

Bibb lettuce seed (Lot No. 58387) were obtained from Charles H. Lilly Co., Portland, Oreg.

Method

Prickly lettuce seeds were gathered in the fall of 1987 from field plots 15 km south of Lewiston, Id. treated with sulfonylurea herbicides and also from an area near Troy, Id. that never had been treated with sulfonylurea herbicides (Mallory-Smith, et al., Weed Technol. (1990) H: (in press). Seeds were planted in a greenhouse soil mix (75% Manitoba peat, 15% perlite, and 10% vermiculite) in 440-ml styrofoam cups and germinated in a growth chamber at 18° C. Seedlings were transplanted into 4.4L containers when they had 3 to 5 leaves. The plants were grown to maturity in a greenhouse under the following conditions: 16-hr photoperiod with a combination of high pressure sodium and multiple vapor halogen lights, and a temperature range of 15°–27° C. Subsequent generations were grown under the same greenhouse conditions as the parents.

For crossing, a susceptible biotype or Bibb lettuce pollen acceptor flowers were selected when the petals either were just visible or had opened slightly. These flowers were sprayed two or three times with a fine stream of distilled water to remove the pollen (Oliver, "New methods of plant breeding," U.S. Bureau Plant Ind. (1910) Bulletin 167). The flowers were air dried. An open flower from the resistant biotype was used as the pollen donor. Pollen was placed on the pollen acceptor flowers by brushing the anthers against the stigma of the washed flower. Reciprocal crosses were made using the susceptible biotype as the male parent. Mature seeds were collected by hand from individual crosses and placed in dry storage at room temperature.

Prickly lettuce is an obligate self-fertilizing species (Ryder, "Lettuce breeding," Breeding Vegetable Crops, edited by M. J. Bassett AVI Publishing Co., Westport, Conn. (1986) pp 436–472). Since it was not possible to visually ascertain if a successful cross had been made, it was necessary to treat the $F_1$ seedlings with metsulfuron to determine if the resistance trait had been crossed into the susceptible biotype. Those plants that survived the treatment were considered to be successful crosses. Since there was no marker, it was impossible to distinguish successfully crossed individuals from self-fertilized individuals in the reciprocal crosses (S biotype as pollen donor) and the screening technique could not be used to determine if the cross had been made because the selfed individuals would be resistant as well as the hybrids.

In order to test the effects of herbicide treatment, plants were grown under the conditions previously described. At least 100 plants were used in each study. A 30 ml 500 ppb ai w/v metsulfuron foliar and soil drench treatment was applied at the 2 to 3 leaf stage of growth to the parents (resistant=R, susceptible=S), the $F_1$ generation and the $F_2$ population of the S×R cross. The $F_2$ population of the Bibb×R cross and the $F_3$ populations of both crosses were treated with 13 g ai/ha (3 times the commercial rate) of metsulfuron applied through a custom built [CO2] $CO_2$ pressurized greenhouse spray chamber. Treatments were applied at 275 kPa, 300 L/ha, and 2.5 km/h. A non-ionic surfactant (octyl phenoxy polyethoxy ethanol, 90% ai) at 0.5% v/v was added to all herbicide treatments.

The $F_1$ plants that survived the herbicide treatment were transplanted into 4.4L containers and allowed to self to produce $F_2$ seed. The $F_2$ seedlings in the 3 to 5 leaf stage were treated with herbicide as described previously. The plants were scored as susceptible (S), intermediate (I) or resistant (R) in their response to metsulfuron. The $F_{2's}$ scored as I or R were transplanted into 4.4L containers and grown to maturity for $F_3$ seed production. The herbicide treated $F_3$ population was evaluated for segregation of the resistance trait. The best fit for Chi-Square analysis of the $F_2$ generation of both crosses was a 1:2:1 ratio indicating the trait was controlled by a single nuclear gene with incomplete dominance (Tables 7 and 8).

TABLE 7

Chi-Square Analysis for the $F_2$ Generation Susceptible by Resistant Prickly Lettuce Biotype Cross

| Ratio | Exp | Obs | $X^2$ |
|---|---|---|---|
| 1 | 29 | 25 | 0.5517 |
| 2 | 58 | 66 | 1.1034 |
| 1 | 29 | 25 | 0.5517 |
| | | | $X^2 = 2.2068$ |
| | | | $0.25 < P < 0.50$ |

TABLE 8

Chi-Square Analysis for the $F_2$ Generation Bibb Lettuce by Resistant Prickly Lettuce Biotype Cross

| Ratio | Exp | Obs | $X^2$ |
|---|---|---|---|
| 1 | 20.75 | 22 | 0.0753 |
| 2 | 41.50 | 41 | 0.0060 |
| 1 | 20.75 | 20 | 0.0271 |
| | | | $X^2 = 0.1084$ |
| | | | $0.90 < P < 0.95$ |

The $F_3$ generations of both crosses were evaluated to confirm the results of the $F_2$ Chi-Square. Seeds from these $F_2$ S×R prickly lettuce plants scored as resistant produced seedlings that were resistant to the 13 g/ha treatment of metsulfuron. Of the 116 seedlings treated, one showed symptoms and one died. Prickly lettuce plants rated as intermediate in the $F_2$ generation produced seedlings which segregated as expected with approximately one-fourth of the seedlings susceptible and three-fourths of the seedlings intermediate or resistant ($X^2$=3.36, 0.05<P<0.10). The $F_3$ generation of the Bibb×R cross responded the same as the prickly lettuce $F_3$ generation with the seedlings from the R plants all surviving with no symptoms and the seedlings from the I plants segregating 1:2:1 ($X^2$=0.28, 0.75<P<0.90).

The response of the $F^3$ generation supports the hypothesis that the R plants were homozygous for the resistance trait and the I plants were heterozygous for the trait. These results are similar to those reported in the literature for resistant plants produced by mutagenesis where the trait has been reported to be either dominant (Haughn et al., "Sulfonylurea-resistant mutants of Arabidopsis thaliana," Mol. Gen. Genet. (1986) 204:430–434) or semidominant (Chaleff et al., "Herbicide-resistant mutants from tobacco cell cultures," Science (1984) 223:1148–1151).

2. Prizehead Lettuce

Domestic head lettuce var. Prizehead (Lot No. 68319) seed were obtained from Charles H. Lilly Co., Portland, Oreg. Incorporation of sulfonylurea herbicide resistance into domestic prizehead lettuce was accomplished as shown in the following schematic.

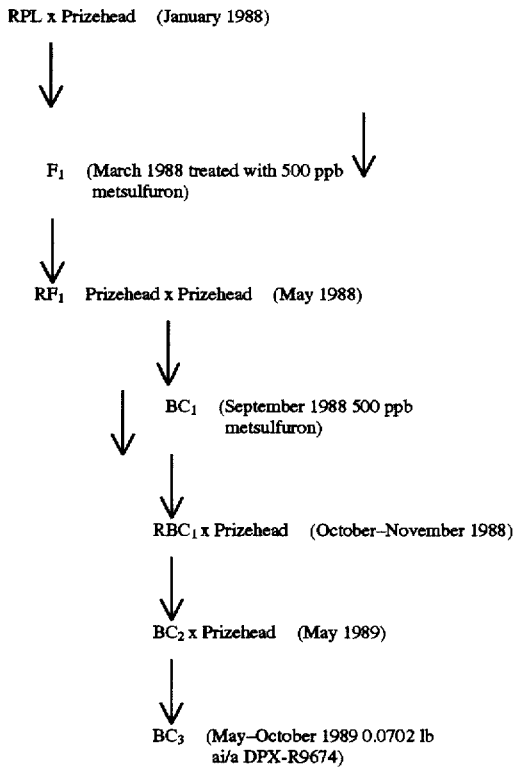

The methods used to obtain transgenic plants were as described above for Bibb lettuce.

3. Grand Rapids Lettuce

Domestic leaf lettuce var. Grand Rapids seed (Lot No. 68180) were obtained from Charles H. Lily Co., Portland, Oreg. Incorporation of sulfonylurea herbicide resistance into domestic Grand Rapids lettuce was accomplished as shown in the following schematic.

RPL x Grand Rapids (January 1988)

↓

$F_1$ (March 1988 500 ppb metsulfuron)

↓

$RF_1$ Grand Rapids x Grand Rapids (May 1988)

↓

$RBC_1$ x Grand Rapids (January–March ppb metsulfuron)

↓

$RBC_1$ x Grand Rapids (May 1989)

↓

$BC_2$ (discontinued because germination was erratic and slow)

Grand Rapids seed (Lot 68180) were obtained from Charles H. Lilly Co., Portland, Oreg.

The methods used to obtain transgenic plants were as described above for Bibb lettuce.

4. Vanguard Lettuce

Incorporation of sulfonylurea herbicide resistance into domestic Vanguard lettuce was accomplished as shown in the following schematic.

V x RBC3 (B3xB6xP7–10A) (November 1989)

↓

$F_1$ (November 1989 0.0792 lb ai/a DPX-R9674)

Vanguard seed obtained from Asgrow Seed Company, P.O. Box L, San Juan Bautista, Calif. 95045.

The methods used to obtain transgenic plants were as described above for bibb lettuce.

5. Ithica Lettuce

Incorporation of sulfonylurea herbicide resistance into domestic lettuce var. Ithica was accomplished as shown in the following schematic.

1×$RBC_3$ (November 1989)

Ithica seed were obtained from Asgrow Seed Company, P.O. Box L, San Juan Bautista, Calif. 95045.

The methods used to obtain transgenic plants were as described above for Bibb lettuce.

6. Empire Lettuce

Incorporation of sulfonylurea herbicide resistance into domestic lettuce var. Empire was accomplished as shown in the following schematic.

E x $RBC_3$ (November 1989)

↓

$F_1$ (December 1989 0.0792 lb/a DPX-R9674)

Empire seed were obtained from Asgrow Seed Company, P.O. Box L, San Juan Bautista, Calif. 95045. The methods used to obtain transgenic plants were as described above for Bibb lettuce.

7. Salinas Lettuce

Incorporation of sulfonylurea herbicide resistance into domestic lettuce var. Empire was accomplished as shown in the following schematic.

S x $RBC_3$ (November 1989)

↓

$F_1$ (December 1989 0.0792 lb/a DPX-R9674)

Salinas seed were obtained from Asgrow Seed Company, P.O. Box L, San Juan Bautista, Calif. 94045.

The methods used to obtain transgenic plants were as described above for Bibb lettuce.

EXAMPLE 3

Field Performance of Resistant Bibb Lettuce

A study was established in order to evaluate $BC_2$ (Bibb× Sulfonylurea Herbicide Resistant Prickly Lettuce crosses) and parent Bibb plants responses to DPX-R9674 in a field situation. Transgenic plants and parent Bibb lettuce plants were transplanted into the field in a randomized complete block design with four replications. Each plot contained 10 plants. Two rates of DPXR9674, 0.0313 and 0.0939 lb ai/a, were applied after the plants became established in the field.

$BC_2$ plants were evaluated visually and rated as susceptible or resistant in their response to the herbicide (Table 9). The plants segregated 3:1 as was expected based on previous greenhouse studies. The resistance trait is inherited as a single, nuclear gene with incomplete dominance. The plants responded the same in the field as they had in the greenhouse.

TABLE 9

Chi-Square Analysis for the $BC_2$ × Prickly Lettuce Cross

| Ratio | Exp | Obs | $X^2$ |
|---|---|---|---|
| 1 | 17.5 | 19 | 0.057 |
| 3 | 52.5 | 51 | 0.019 |
| | | | 0.076 |
| | | | $0.7 < P < 0.9$ |

Hybrid crop plants have been obtained having resistance to sulfonylurea herbicides which will allow them to be grown in rotation with crops for which sulfonylurea herbicides are the treatment of choice for weed control. Additionally, seed producers will be able to maintain varietal purity between resistant and susceptible lettuce varieties.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. [A] *An herbicide resistant* Lactuca [sativa] plant selected from the group consisting of (1) a plant [retardant] *resistant* to sulfonylurea herbicides, (2) a plant resistant to imidazolinone herbicides, and (3) *sulfonylurea or imidazolinone herbicide resistant* progeny plants of either of plant (1) or plant (2)[;] wherein said plant or [a parent] *an ancestor* of said plant was grown from seed obtained by crossbreeding a Lactuca serriola plant resistant to an herbicide selected from the group consisting of (1) sulfonylurea herbicides and (2) imidazolinone herbicides, with a Lactuca sativa plant.

2. The *herbicide resistant Lactuca* plant according to claim 1, wherein said Lactuca sativa plant is of the variety Bibb, Grand Rapids, Prizehead, Vanguard, Ithaca, Empire or Salinas.

3. A seed of [a] *an herbicide resistant* Lactuca [sativa] plant, said seed obtained from a plant selected from the group consisting of (1) [a] *an herbicide resistant* plant according to claim 1 and (2) progeny of [a] *an herbicide resistant* plant according to claim 1.

4. The seed according to claim 3, wherein said Lactuca sativa plant is of the variety Bibb, Grand Rapids, Prizehead, Vanguard, Ithaca, Empire or Salinas.

5. A plant cell of [a] *an herbicide resistant* Lactuca [sativa] plant and progeny cells of said [cells] *plant cell*, said plant cell obtained from a plant selected from the group consisting of (1) [a] *an herbicide resistant Lactuca* plant according to claim 1 and (2) progeny of [a] *an herbicide resistant Lactuca* plant according to claim 1.

6. The plant cell according to claim 5, wherein said Lactuca sativa is of the variety Bibb, Grand Rapids, Prizehead, Vanguard, Ithaca, Empire or Salinas.

7. A plant comprising cells according to claim 5, and progeny plants derived from said plant.

8. Seeds from [a] *an herbicide resistant Lactuca* plant according to claim [2] *1*.

* * * * *